(12) United States Patent
Mulhauser et al.

(10) Patent No.: US 6,580,945 B2
(45) Date of Patent: Jun. 17, 2003

(54) DEFIBRILLATOR USING LOW IMPEDANCE HIGH CAPACITANCE DOUBLE LAYER CAPACITOR

(75) Inventors: Daniel F. Mulhauser, Windham, NH (US); Al Langguth, Hudson, NH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 140 days.

(21) Appl. No.: 09/812,922

(22) Filed: Mar. 20, 2001

(65) Prior Publication Data

US 2002/0138103 A1 Sep. 26, 2002

(51) Int. Cl.[7] ................................................. A61N 1/39
(52) U.S. Cl. .......................................................... 607/5
(58) Field of Search ............................. 607/5–7, 12, 10

(56) References Cited

U.S. PATENT DOCUMENTS

| | | | | |
|---|---|---|---|---|
| 5,405,361 A | * | 4/1995 | Persson | 607/5 |
| 5,411,525 A | * | 5/1995 | Swanson et al. | 607/5 |
| 5,455,999 A | | 10/1995 | Weiss et al. | |
| 5,484,452 A | * | 1/1996 | Persson | 607/5 |
| 5,507,781 A | * | 4/1996 | Kroll et al. | 607/7 |
| 5,591,212 A | | 1/1997 | Keimel | 607/5 |
| 5,733,309 A | * | 3/1998 | Kroll et al. | 607/5 |
| 5,836,973 A | * | 11/1998 | Kroll | 607/5 |
| 5,849,025 A | | 12/1998 | Owens et al. | |
| 5,978,204 A | | 11/1999 | Stevenson | |
| 6,035,235 A | | 3/2000 | Perttu et al. | |
| 6,141,584 A | | 10/2000 | Rockwell et al. | |
| 6,456,877 B1 | * | 9/2002 | Fishler | 607/5 |

FOREIGN PATENT DOCUMENTS

| | | | | |
|---|---|---|---|---|
| EP | 0587939 A1 | 3/1994 | | A61N/1/362 |
| EP | 1093829 | * | 4/2001 | |
| EP | 1093829 A1 | 4/2001 | | A61N/1/39 |
| JP | 1-160568 | * | 6/1989 | |
| SU | 516405 A | 6/1976 | | A61N/31/00 |
| WO | WO9622811 | 8/1996 | | A61N/1/39 |

* cited by examiner

Primary Examiner—John A. Jeffery (57) ABSTRACT

A low impedance high capacitance double layer capacitor (also known as a "super cap") is used to supply energy to charge a high voltage capacitor. Upon a command from a controller and/or an operator, the high voltage capacitor administers a shock to a patient in order to treat ventricular fibrillation. If a power source is used to augment the double layer capacitor in supplying energy to the high voltage capacitor, the power source charges the capacitor during a dwell time, which is a time between shocks or at start up. Once the decision is made to administer a shock, the high voltage capacitor is charged by the high voltage capacitor and the power source. By adjusting the energy stored in the high voltage capacitor through a voltage limiting device such as a switch mode converter current source, the draw on the power source can be reduced while allowing for a reduced dwell time without affecting the performance of the defibrillator. The use of a double layer capacitor can be used to supply energy to charge a high voltage capacitor without the power supply, and is useful in external and internal defibrillators, and can be used in leadless paddles to allow the operator the greatest freedom of movement.

29 Claims, 9 Drawing Sheets

DEFIBRILLATOR USING LOW IMPEDANCE HIGH CAPACITANCE DOUBLE LAYER CAPACITOR

BACKGROUND OF THE INVENTION

Description of the Related Art

A cardiac arrest is a disruption of the heart's functioning that causes a lack of blood flow to vital organs. The majority of cardiac arrests are associated with a heart arrhythmia such as ventricular fibrillation. During ventricular fibrillation, the normal rhythmic ventricular contractions are replaced by rapid and irregular twitching that results in ineffective and severely reduced pumping of the heart. One method of treating ventricular fibrillation is to use a defibrillator to administer shocks to a patient's heart in order to restore the normal rhythmic ventricular contractions.

There are multiple types of defibrillators, each used for different purposes. Internal defibrillators are implanted in the patient and are used to prevent ventricular fibrillation and regulate the heart rhythms. External defibrillators are used by paramedics and hospitals in order to treat ventricular fibrillation after the occurrence of a heart attack. External defibrillators often have numerous additional features, such as smaller ECG units, that aid in treating the patient and evaluating the factors used in administering shocks. The external defibrillators can be fully automatic, semi-automatic, or manual, depending on the end operator. The more automatic a defibrillator, the greater the role of a controller within the defibrillator plays in administering treatment.

These defibrillators can be portable, such as those used by paramedics and EMS personnel, or attached to carts such as those found in clinics and hospitals. One such portable external defibrillator is disclosed in U.S. Pat. No. 6,141,584 to Rockwell et al., which is commonly assigned and the disclosure of which is incorporated herein by reference.

Figure 1:
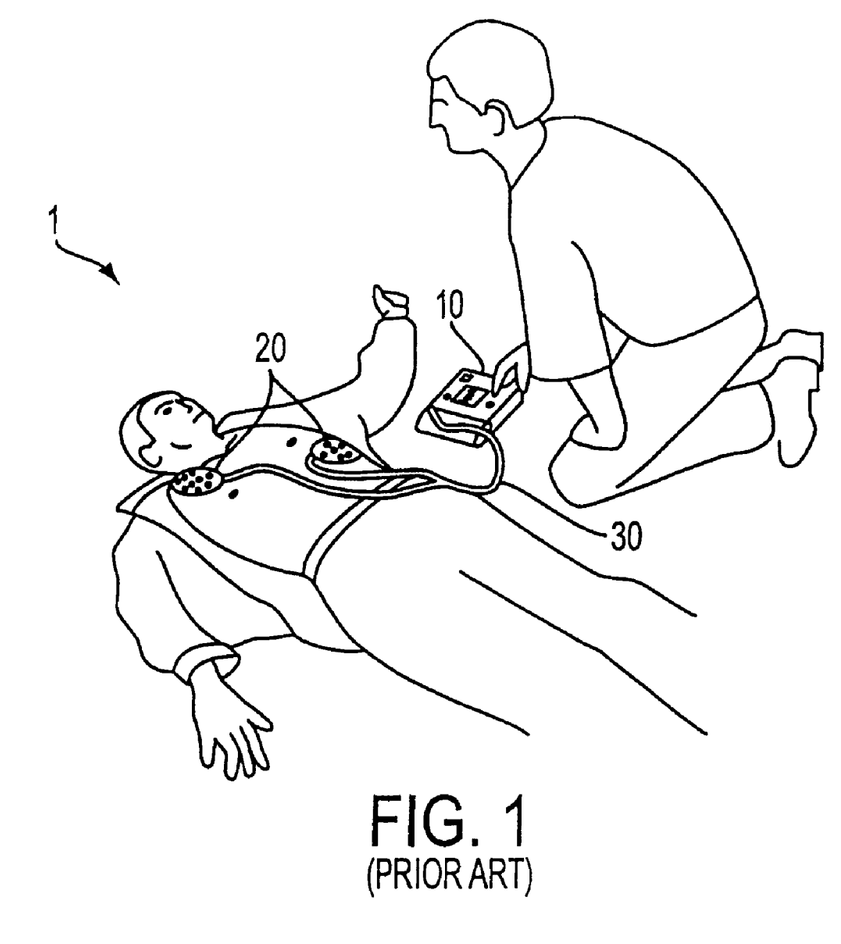
FIG. 1 shows a conventional defibrillator system being used by an operator to administer treatment to a patient.
Figure 2:
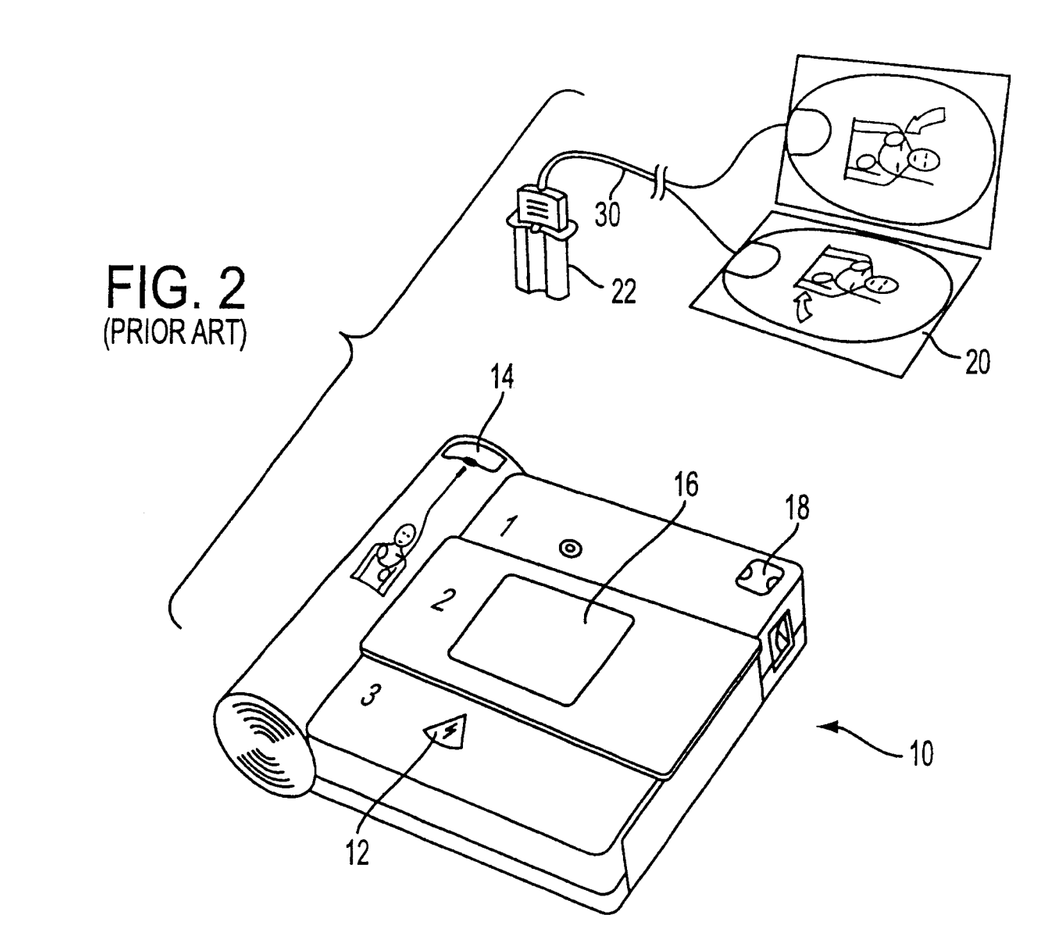
FIG. 2 shows a conventional portable external defibrillator system including a defibrillator and a set of paddles or pads attached by leads.

As shown in FIG. 1, a defibrillator system 1 includes a defibrillator 10 which administers a shock to the patient through paddles/electrodes 20. As shown in FIG. 2, the paddles 20 are connected to a connector 22 by leads 30. The connector 22 is inserted into socket 14 in order to deliver the charge from the defibrillator 10 to the paddles 20. In order to direct the defibrillator 10 to administer the shock, the operator presses a shock button 12 that is located on the defibrillator 10.

In addition, the defibrillator 10 also has a display 16 that is used by the operator to view ECG information or other information useful in the caring for and monitoring of the progress of the patient. The ECG information, which provides information on the condition of the patient's heart, is received through the paddles 20 that also provide the shock to the patient. Since the shown the defibrillator 10 is portable, it has a battery charge indicator 18 so that the operator can assess the ability of the defibrillator 10 to continue to administer treatment to the patient.

In operation, when a patient goes into cardiac arrest, the electrodes 20 are applied across the chest of the patient in order to acquire the ECG signal from the patient's heart. The ECG information is displayed to the operator on the display 16. In a manual defibrillator, the operator determines from the ECG information whether to administer the shock. For automatic and semiautomatic defibrillators, the defibrillator 10 aids in this determination to varying degrees.

However determined, if ventricular fibrillation is to be treated with the defibrillator system 1, the operator applies the paddles 20 to the patient and presses the shock button 12. The defibrillator administers the shock through the paddles 20 to the patient in order to restore the normal rhythm of the heart. The defibrillator 10 is then used to again assess the condition of the patient, and to administer further treatments based on the detected ECG signal. In general, only three such treatments are provided with any likelihood of success.

Figure 3:
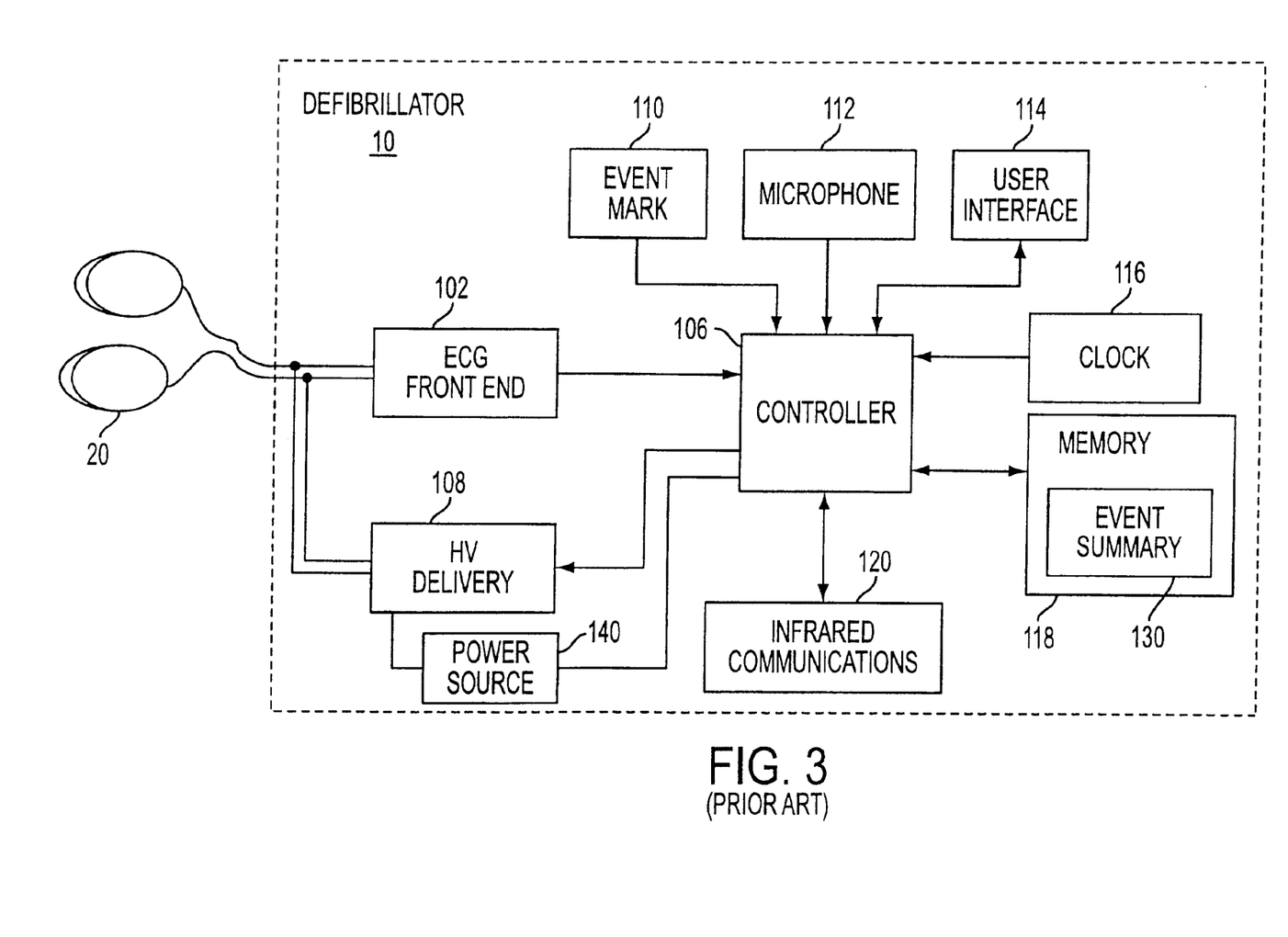
FIG. 3 is a schematic representation of a conventional defibrillator.

FIG. 3 is a schematic representation of the defibrillator 10. The paddles 20 provide an ECG signal to the ECG front end 102, which provides the ECG signal to a controller 106 for evaluation and display to the operator via a user interface 114. This information is also stored by the controller 106 in a memory 118. Also stored in the memory 118 is an event summary 130, in which information from an event mark 110, a microphone 112, and/or from a clock 116 are stored. This information is useful during a transfer (often called a handoff) between the hospital and the clinic in order to continue the treatment of the patient. In the device shown, an infrared communications port 120 is provided to communicate the information in memory 118 with an outside device during the transfer.

In addition, a power source 140 is provided in order to power the entire defibrillator 10. The power source 140 can be a line source or a battery, or any similar device which provides sufficient power to provide the shock and the ECG monitoring functions described herein. For portable defibrillators such as that shown, a battery is typically used for the power source 140. This battery may be disposable, or rechargeable.

A high voltage (HV) delivery device 108 administers the shock to the patient via the paddles 20 at the command of the controller 106. At the command of the operator using the shock button 12, the charge from the high voltage delivery device 108 is administered to the patient in order to bring about the normal rhythmic ventricular contractions. The power supply 140 supplies the charging energy to the high voltage delivery device 108 during a charging time in order to store sufficient energy to administer a treatment. This charging time is preferably small since the rapid administration of the treatments is desirable in order to produce a favorable result.

Figure 4:
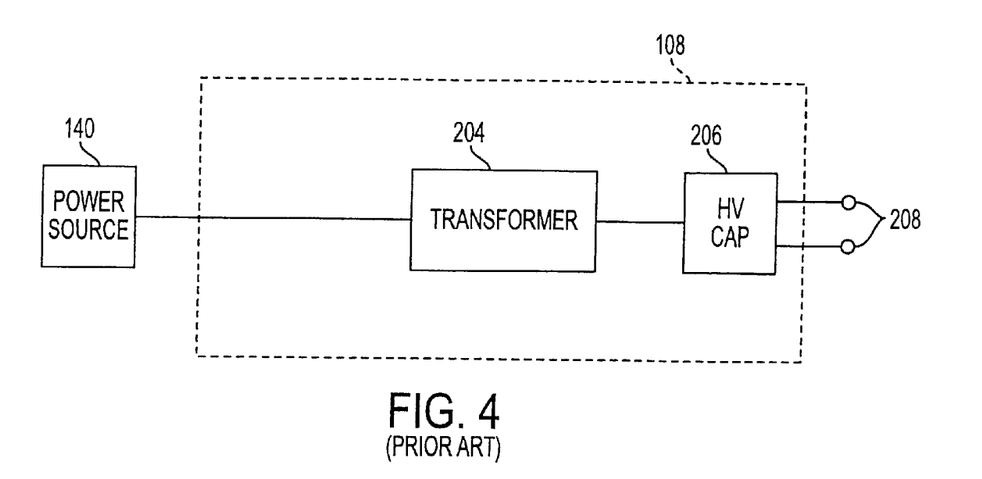
FIG. 4 is a schematic representation of a conventional high voltage delivery device.

As schematically shown in FIG. 4, the high voltage delivery device 108 has two major components: a transformer 204 and a high voltage capacitor 206 (i.e., "HV cap"). When in operation, the power source 140 provides power through the transformer 204 to charge the HV cap 206. The HV cap 206 stores the required voltage to be administered on the command of the operator or a controller 106 shown in FIG. 3. The HV cap 206 is typically a 105 $\mu$f capacitor, and is capable of delivering a charge of 2100 volts to the patient through terminals 208 to the paddles 20 shown in FIG. 3. After discharge, the HV cap 206 is then recharged by the power source 140 if there is a continued need for defibrillation treatment.

Figure 5:
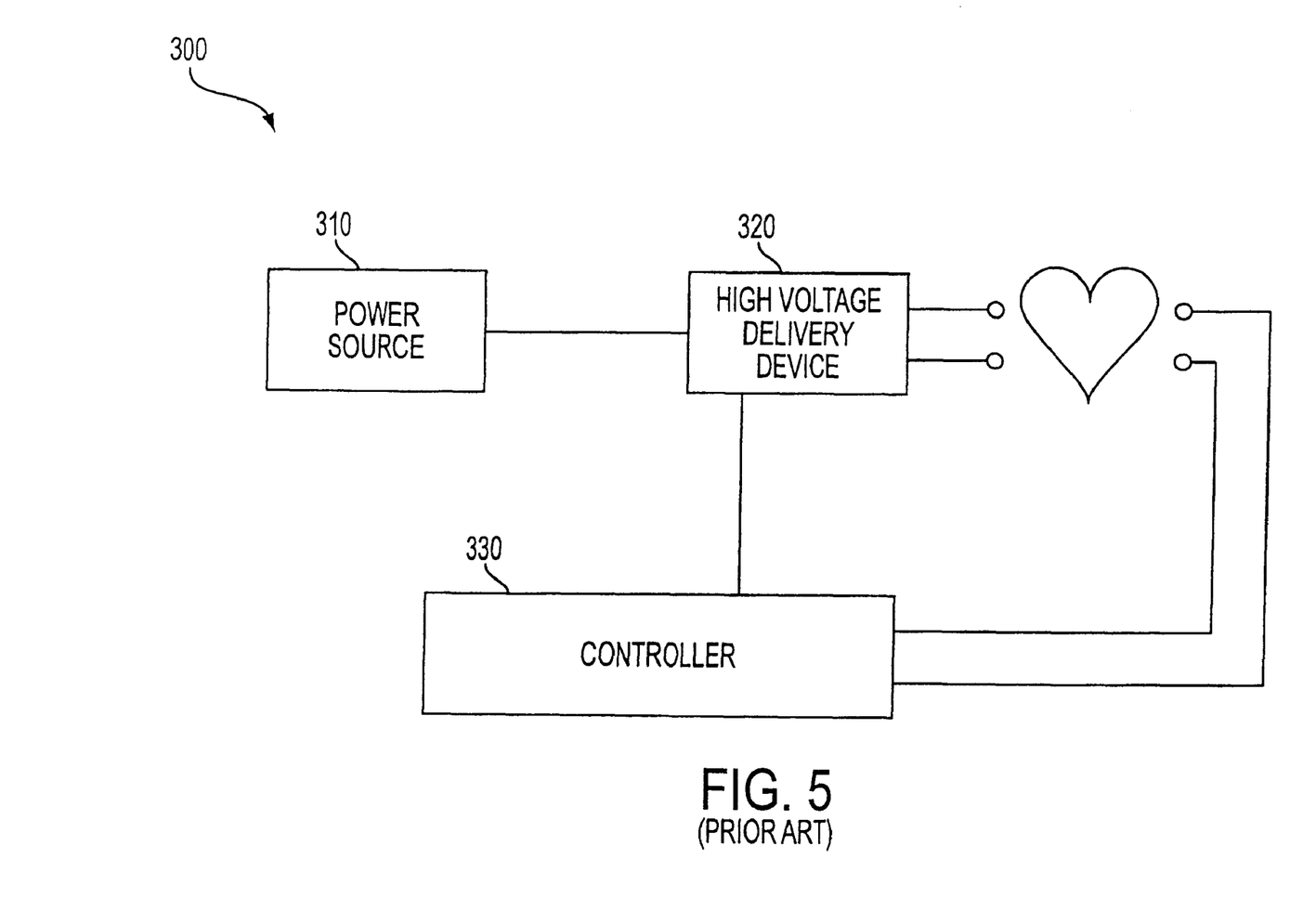
FIG. 5 is a schematic representation of a conventional internal defibrillator.

A second type of defibrillator is an internal defibrillator. Internal defibrillators use a similar process for charging an HV cap. As shown in FIG. 5, an internal defibrillator 300 uses a power source 310 to charge a high voltage delivery device 320, which is a similar structure to the high voltage delivery device 108 shown in FIG. 4. The controller 330 controls the discharge of the high voltage delivery device 320 through the heart in order to regulate the rhythm of the heart. Where multiple capacitors are used in the high voltage delivery device 320, the high voltage delivery device 320 further includes an H-bridge in order to selectively provide shocks from the individual capacitors to the patient. In addition, the power source 310 is often a battery. An example of one such known internal defibrillator is found in U.S. Pat. No. 6,035,235 to Perttu et al.

A drawback to the conventional defibrillator designs, both external and internal, is the need for larger power sources to charge the HV cap in order to provide the necessary shock. For certain external defibrillators, especially those used in clinics, a line voltage can be supplied instead of a battery. However, such line sources limit the portability of these defibrillators when used in confined spaces.

Figure 6:
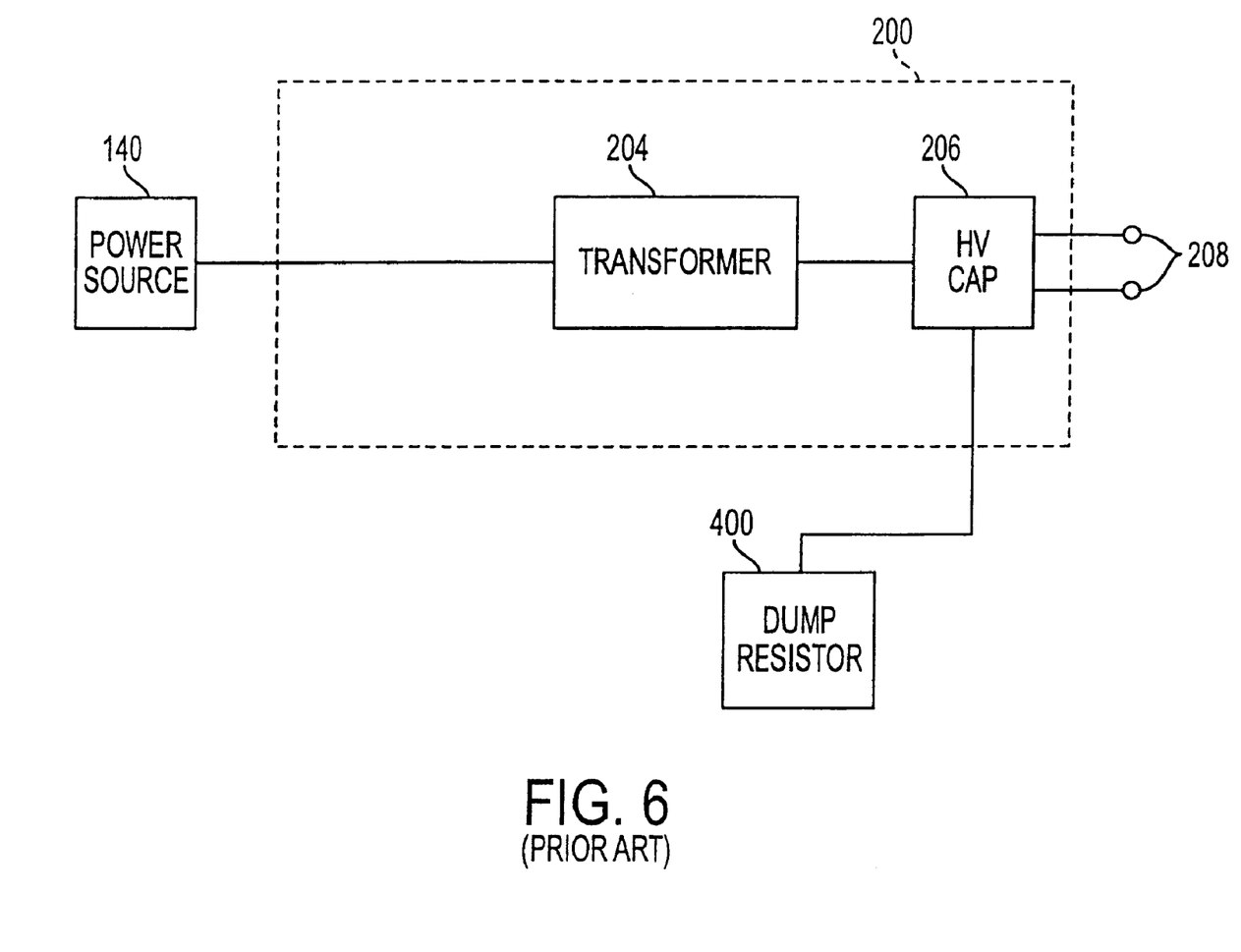
FIG. 6 is a schematic representation of a conventional high voltage delivery device including a dump resistor.

A further problem encountered during the use of a defibrillator device is how to discharge or otherwise dissipate energy from the high voltage delivery device when the stored energy is not to be applied to a patient. As shown in FIG. 6, a common solution is to employ a dump resistor 400. In essence, the voltage from a high voltage delivery device 200 is dissipated as heat by the dump resistor 400, which is basically a large resistor. A problem encountered with this energy dissipation device is that it releases large amounts of heat. Such releases, especially if repeated in a short time, could damage the defibrillator.

SUMMARY OF THE INVENTION

An embodiment of the present invention has a defibrillator comprising a power source, a low impedance high capacitance double layer capacitor that stores energy from the power source, and a high voltage capacitor that stores energy provided the double layer capacitor, and discharges the stored energy to a patient.

In another embodiment of the present invention, the high voltage capacitor stores energy provided jointly by the double layer capacitor and the power source.

In another embodiment of the present invention, the defibrillator is located internal to a patient.

In another embodiment of the present invention, a set of leadless paddles or pads houses the high voltage capacitor and the double layer capacitor in order to defibrillate the patient without leads.

In another embodiment of the present invention, a method of charging a high voltage capacitor in a defibrillator is provided that includes supplying energy to a low impedance high capacitance double layer capacitor using a power source during a first time, and supplying energy from the low impedance high capacitance double layer capacitor to the high voltage capacitor during a second time.

In a yet further embodiment of the present invention, a method of administering a charge from a defibrillator to a patient is provided, including supplying energy to a low impedance high capacitance double layer cap using a power source during a first time, supplying energy from the low impedance high capacitance double layer cap to the high voltage capacitor during a second time, and discharging the high voltage capacitor to administer the charge to the patient.

BRIEF DESCRIPTION OF THE DRAWINGS

These and other objects and advantages of the invention will become apparent and more readily appreciated from the following description of the preferred embodiments, taken in conjunction with the accompanying drawings of which.

DESCRIPTION OF THE PREFERRED EMBODIMENTS

Reference will now be made in detail to the present preferred embodiments of the present invention, examples of which are illustrated in the accompanying drawings, wherein like reference numerals refer to the like elements throughout. The embodiments are described below in order to explain the present invention by referring to the figures.

Figure 7:
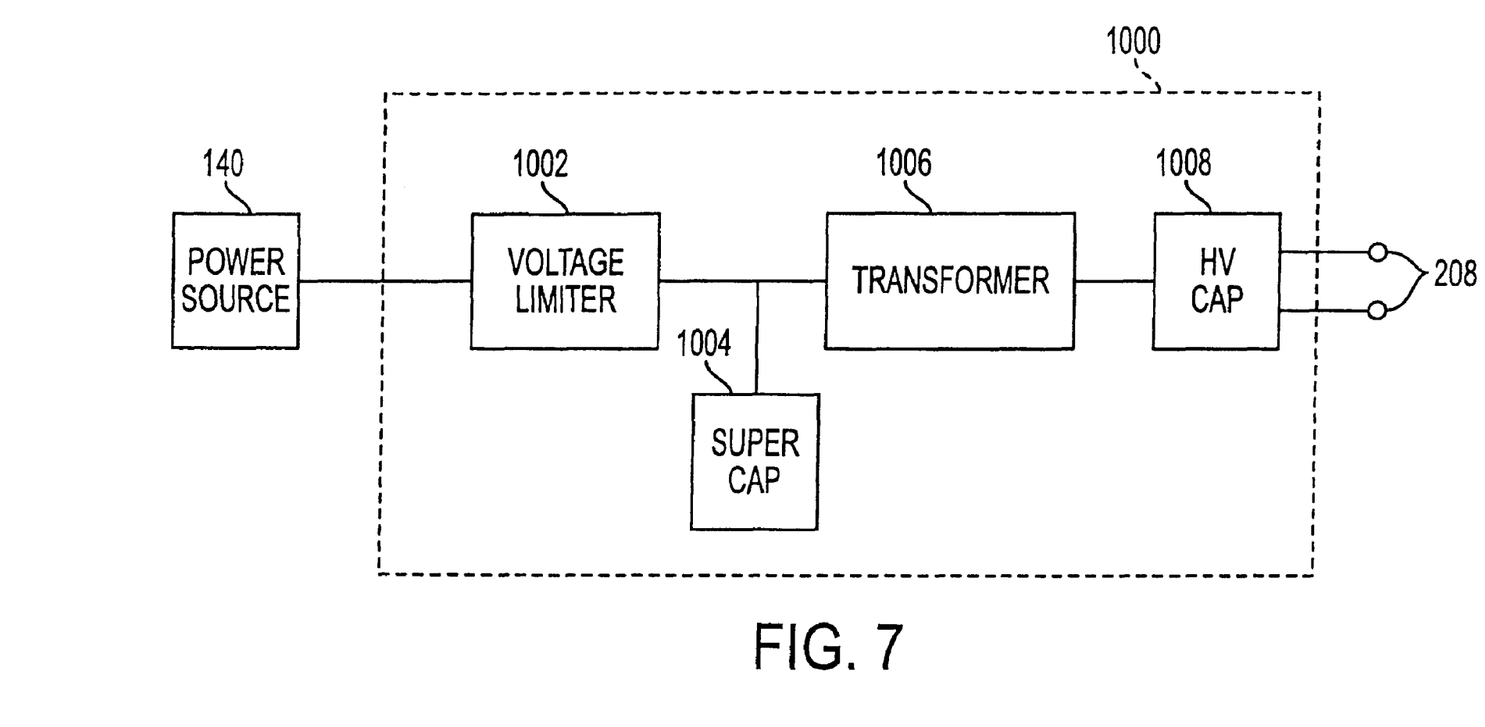
FIG. 7 is a schematic representation of a high voltage delivery device according to an embodiment of the present invention.

As shown in FIG. 7, a high voltage delivery device 1000 according to an embodiment of the present invention comprises a voltage limiter 1002, a low impedance high capacitance double layer capacitor 1004 (i.e., "DL cap"), a transformer 1006, and a high voltage capacitor 1008 (i.e., "HV cap"). The high voltage delivery device 1000 is suitable for use in either an external defibrillator, such as that disclosed in FIG. 2 or in an internal defibrillator, such as that shown in FIG. 5.

The power source 140 provides energy via the voltage limiter 1002 to the DL cap 1004. The voltage limiter 1002 is a switch mode converter current source that is used to limit the current, and hence the rate energy is drawn from the power source 140 and eventually the voltage stored in the DL cap 1004 over time. However, any mechanism that limits voltage can be used. Further, if there is no need to limit the voltage, the voltage limiter 1002 need not be used.

The DL cap 1004 is has one or more capacitors typically known as super caps or double layer caps, and has a low equivalent series resistance (ESR), a low impedance, and a high capacitance on the order of farads, tens of farads, or hundreds of farads. In the shown embodiment, sixteen total super caps are used within the DL cap 1004. These super caps are arranged with eight in series by two in parallel. One such super cap that would be useful in this application is the Maxwell PC-10 capacitor. It is also possible that the DL cap 1004 can comprise a larger super cap instead of multiple smaller super caps.

It is further preferable that the first time constant of the discharge of the super cap would be used to allow more energy to be removed faster.

When in operation, the defibrillator is turned on, and the power source 140 stores energy in the DL cap 1004, with the amount of voltage regulated by the voltage limiter 1002. When the high voltage delivery device 1000 is to be discharged into a patient via terminals 208, the energy stored in the DL cap 1004 and the energy available from the power source 140 is jointly used to charge the HV cap 1008 via transformer 1006. On discharge, the HV cap 1008 provides the voltage through the terminals 208 to the patient.

Between discharges, the power source 140 begins to recharge the DL cap 1004. Typically, the charging and recharging of the DL cap 1004 takes place during a dwell time, which is the time after power up or after the discharge up until the point that a decision is made to administer another charge. During this dwell time, the operator or the controller, such as the controller 106 shown in FIG. 3 or the controller 330 shown in FIG. 5, decides if there is a need to administer another shock. After the dwell time, if another shock is to be administered, the HV cap 1008 is again charged using the power source 140 and the DL cap 1004. Using this system, the power source 140 is not required to provide all of the energy to change the HV cap 1008, but is able to jointly provide this energy with the DL cap 1004. This allows the use of a smaller power source 140, or otherwise reduces the draw on the power source 140.

By way of example, if the total energy to be delivered by the HV cap 1008 is 200 Joules, and the time required to charge the HV cap 1008 to 232 Joules is 4 seconds, there is a need for the power source 140 to supply all Joules in these 4 seconds. Using a conventional device such as that shown in FIG. 4, a 77.3 watt power source 140 would be required (given a charge efficiency of 75%). However, using the DL cap 1004 according to an embodiment of the present invention, assuming that the dwell time between the discharges is approximately 6 seconds, a 30.9 watt power supply 140 can build up 185.2 Joules in the DL cap 1004. Thus, when the HV cap 1008 is to be recharged, 77.3 watts of power is jointly available from the power source 140, which has 30.9 watts of power, and the DL cap 1004, which has 46.4 watts of power available. As is evident from this example, a 30.9 watt power supply 140 using a DL cap 1004 is able to provide as much charging power as a 77.3 watt power supply 140, but is smaller, lighter, and cheaper since the power supply 140 itself is smaller.

By way of a second example, the amount of time taken to charge the HV cap 1008 can be dramatically reduced using the DL cap 1004 according to an embodiment of the present invention. For instance, to conventionally charge 309 Joules of energy in the HV cap 1008 with a 30.9 watt line supply or a 14.4 volt battery with a 2.15 amp ability takes 10 seconds. However, if the DL cap 1004 is used, during a 6 second dwell time, 185.2 Joules can be stored in the DL cap 1004 using this same power supply 140. Assuming this 185.2 Joules is removed from the DL cap 1004 during the charging of HV cap 1008 in 4 seconds, the power source 140 need only supply 123.8 Joules in order to jointly provide the required 309 Joules to charge the HV cap 1008 to 232 Joules. As such, using the same 30.9 watt line supply or 14.4 volt battery with a 2.15 amp ability, the HV cap 1008 receives 309 Joules in 4 seconds according to the an embodiment of the present invention instead of 10 seconds using a conventional method.

According to another embodiment of the present invention, the connection between the HV cap 1008 and the DL cap 1004 is symmetrical. In this way, if the charge in the HV cap 1008 is not to administered to the patient, there is no need for a dump resistor 400 shown in FIG. 6 since the undischarged energy may simply be restored from HV cap 1008 to the DL cap 1004. Thus, the HV cap 1008 is discharged without generating heat.

By way of an example of such a symmetrical circuit, if the transformer 1006 is a DC to DC HV converter or flyback converter, these can be made bidirectional by adding a free wheeling diode on the primary side and an additional switch on the secondary side. Thus, when there is a need to shed energy, the converter would be run backwards with the DL cap 1004 storing the energy and allowing the HV caps 1008 to safely discharge.

In addition, if the defibrillator is constructed to sense if the charge in the DL cap 1004 is above a nominal charge, the defibrillator will not use the power source 140 to replenish the energy in the DL cap 1004 until the DL cap 1004 is below this nominal charge. In this way, if the HV cap 1008 discharges to the DL cap 1004, the energy is conserved and the draw on the power source 140 is further reduced.

Figure 8:
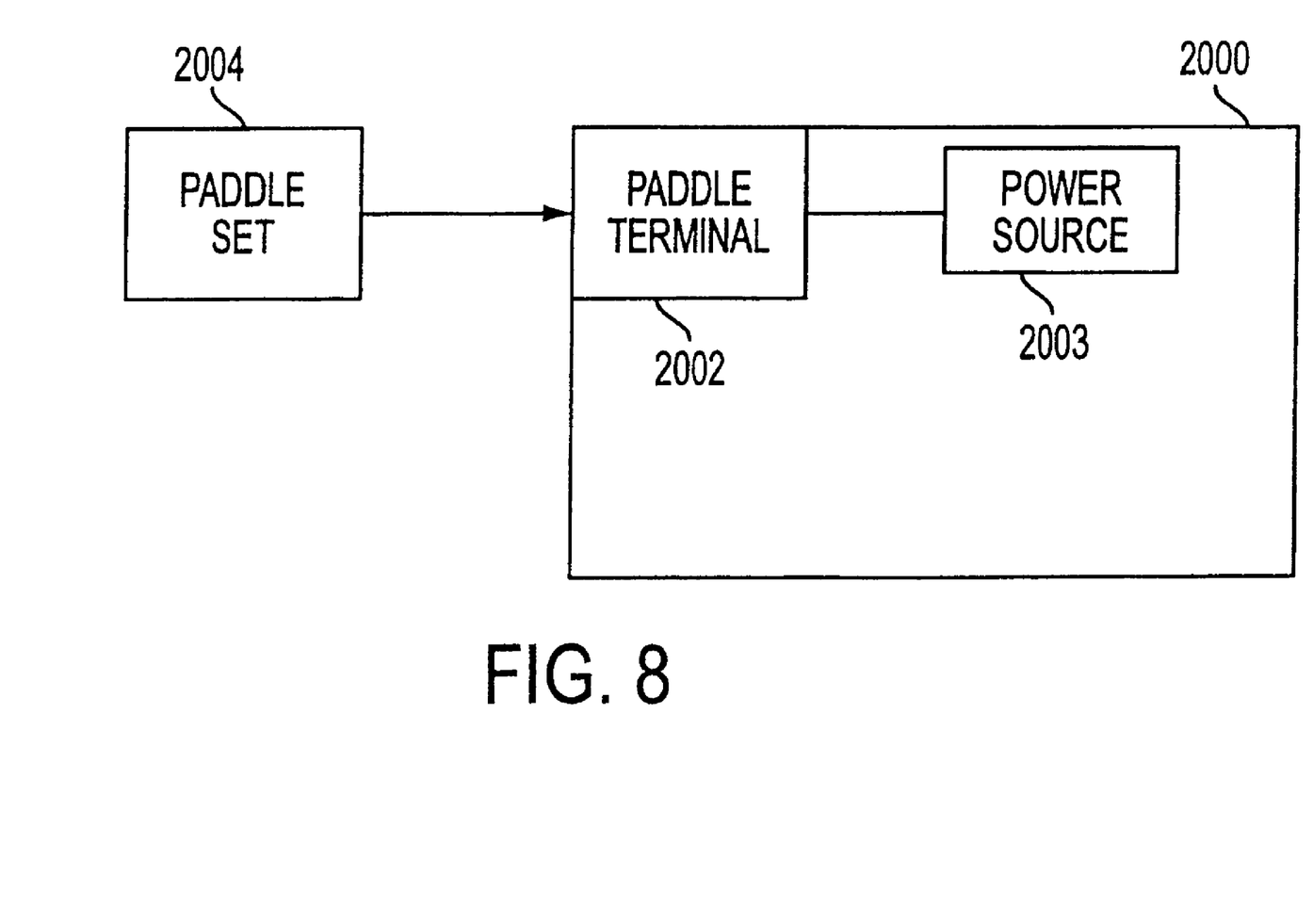
FIG. 8 is a schematic representation of a defibrillator for use with a leadless paddle set according to another embodiment of the present invention.
Figure 9:
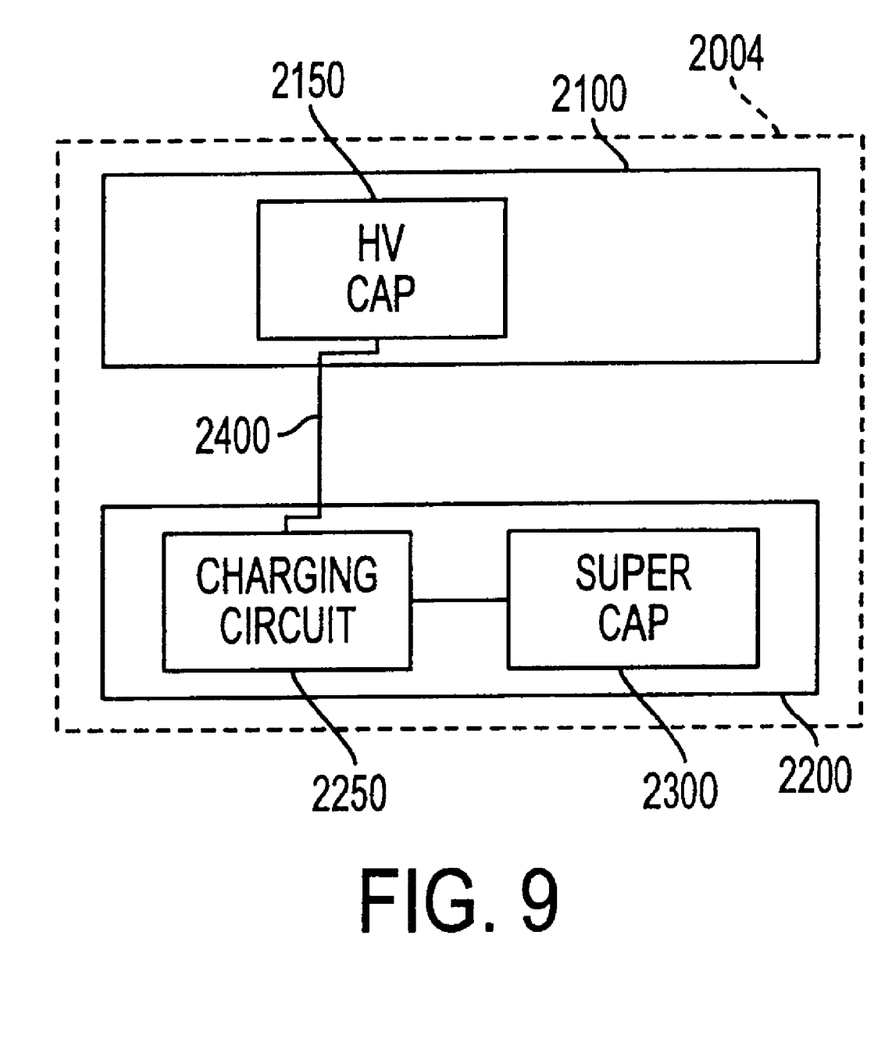
FIG. 9 is a schematic representation of the leadless paddle set including low impedance high capacitance capacitor and high voltage capacitor according to another embodiment of the present invention.

FIGS. 8 and 9 show a leadless paddle defibrillator according to another embodiment of the present invention. As shown, a defibrillator housing 2000 includes a power source 2003 and a paddle terminal 2002. While not shown for the sake of simplicity, this defibrillator housing 2000 can also contain leads to an ECG device or other similar device found in conventional defibrillators such as that shown in FIG. 2.

A leadless paddle set 2004 is accommodated by the paddle terminal 2002 such that, during docking, the power source 2003 provides energy to charge the paddle set 2004. The paddle set 2004 comprises first and second paddles 2100 and 2200. The first paddle 2100 houses a high voltage capacitor 2150 (i.e., "HV cap"). The second paddle 2200 houses a charging circuit 2250 and a low impedance high capacitance double layer capacitor 2300 (i.e., "DL cap"), which uses one or more double layer super caps. The DL cap 2300 provides energy to the HV cap 2150 through wire 2400.

As shown, the DL cap 2300 provides the energy to the HV cap 2150 without the power source 2003. As there is no power source, the DL cap 2300 need to supply more energy than in the embodiment shown in FIG. 7. For instance, instead of using a grouping of Maxwell PC 10 capacitors, Maxwell PC-100 capacitors might be used.

In addition, the DL cap 2300 would typically use multiple super caps, with each super cap being used for a single discharge. These super caps are used with a conventional H-bridge in order to selectively provide energy from individual capacitors to the HV cap 2150.

While not shown, it is understood that additional items might be included in the paddle set 2004, such as transformers, or a transmitter for communicating ECG information and other information to and from the defibrillator housing 2000 to aid in the administration of the treatment. It is further understood that a small power source could also be included in order to jointly provide energy to the HV cap 2150.

The number of super caps in DL cap 2300 is related to the number of expected charges. While, typically, only three charges are performed, an increased number of super caps, such as 8, are provided in order to have a safety margin.

Although a few preferred embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A defibrillator comprising:
   a power source;
   a first capacitor that stores energy from said power source;
   a second capacitor that stores the energy provided by said first capacitor so as to discharge the stored energy to a patient; and a set of paddles to administer a charge from said second capacitor, and wherein said first capacitor and said second capacitor are located in said set of paddles.

2. The defibrillator of claim 1, wherein said second capacitor stores the energy provided jointly by said first capacitor and said power source.

3. The defibrillator of claim 2, further comprising a voltage limiting device that limits a draw on said power source and allows said first capacitor to charge.

4. The defibrillator of claim 3, wherein said voltage limiting device comprises a switch mode converter current source.

5. The defibrillator of claim 4, wherein said power source comprises a line source.

6. The defibrillator of claim 4, wherein said power source comprises a battery.

7. The defibrillator of claim 2, wherein a capacitance of said first capacitor is determined in accordance with an amount of the energy stored by said first capacitor in a dwell time and an ability of said power source to supply the energy to said second capacitor in a charging time.

8. The defibrillator of claim 7, wherein said first capacitor supplies a majority of charging energy to said second capacitor.

9. The defibrillator of claim 2, wherein said first capacitor is symmetrically connected to said second capacitor such that said second capacitor selectively discharges the energy into said first capacitor.

10. The defibrillator of claim 9, further comprising a controller that senses a nominal level of charge in said first capacitor, and provides the energy from said power source to said first capacitor if said first capacitor has less than the nominal level of charge.

11. The defibrillator of claim 2, wherein the defibrillator is located external to the patient, and further comprising a set of paddles or pads that administer a shock resulting from a discharge of said second capacitor through said set of paddles.

12. The defibrillator of claim 1, wherein said first capacitor comprises a low impedance high capacitance double layer capacitor having low equivalent series resistance, and said second capacitor comprises a high voltage capacitor.

13. The defibrillator of claim 12, wherein said first capacitor has a first time constant and supplies energy to said second capacitor during the first time constant.

14. The defibrillator of claim 1, wherein said first capacitor is rated to capacitances of a farad or more.

15. The defibrillator of claim 1, wherein said first capacitor is symmetrically connected to said second capacitor such that said second capacitor selectively discharges the energy into said first capacitor.

16. The defibrillator of claim 15, further comprising a controller that senses a nominal level of charge in said first capacitor, and provides energy from said power source to said first capacitor if said first capacitor has less than the nominal level of charge.

17. The defibrillator of claim 1, wherein the defibrillator is located internal to the patient.

18. The defibrillator of claim 1, wherein said set of paddles comprises first and second paddles, wherein said first capacitor is located in the first paddle and said second capacitor is located in the second paddle.

19. The defibrillator of claim 18, further comprising a housing with a paddle terminal to supply energy to said first capacitor when said set of paddles is docked in the paddle terminal, and wherein said set of paddles comprise leadless paddles that are not connected to said housing.

20. The defibrillator of claim 19, wherein said first capacitor comprises a low impedance high capacitance double layer capacitor having low equivalent series resistance, and said second capacitor comprises a high voltage capacitor.

21. The defibrillator of claim 20, wherein the first or second paddle further comprises a charging circuit that charges said second capacitor.

22. The defibrillator of claim 20, wherein said first capacitor comprises smaller double layer capacitors, and wherein a number of the smaller double layer capacitors is determined in accordance with the number of expected discharges to be administered by the defibrillator.

23. A leadless paddle set for use in a defibrillator having a power source, comprising:
a first capacitor that stores energy from the power source; and
a second capacitor that stores energy provided by said first capacitor, and discharges the stored energy to a patient.

24. The leadless paddle set of claim 23, further comprising a charging circuit to receive energy from the power source, and to provide energy to said first capacitor, wherein the power source is located external to the leadless paddle set.

25. The leadless paddle set of claim 24, further comprising a first paddle and a second paddle connected by wires, wherein said first capacitor and said charging circuit are located in said first paddle and said second capacitor is in said second paddle, and said first capacitor provides energy to said second capacitor through said wires.

26. The leadless paddle set of claim 23, further comprising an internal battery to receive and store energy from, wherein the power source is located external to the leadless paddle set, and wherein said internal battery and said first capacitor provide energy to said second capacitor.

27. The leadless paddle set of claim 23, further comprising a first paddle and a second paddle connected by wires, wherein said first capacitor is located in said first paddle and said second capacitor is in said second paddle, and said first capacitor provides energy to said second capacitor through said wires.

28. The leadless paddle set of claim 23, further comprising a wireless communications port to communicate data detected by the leadless paddle set to a main defibrillator.

29. A defibrillator comprising:
a housing comprising a power source and a paddle terminal;
first and second leadless paddles that are not connected to said housing, but are sized to be accommodated in the paddle terminal;
a low impedance high capacitance double layer capacitor having low equivalent series resistance located in said first paddle, said double layer capacitor stores energy from the power source when said first paddle is docked in the paddle terminal, said double layer capacitor comprising smaller double layer capacitors, wherein a number of the smaller double layer capacitors is determined in accordance with the number of expected discharges to be administered by the defibrillator;
a high voltage capacitor located in said second paddle, said high voltage capacitor stores the energy provided by said double layer capacitor so as to discharge the stored energy to a patient; and
a charging circuit located in said second paddle, said charging circuit charges said high voltage capacitor.

* * * * *